United States Patent [19]

Ensor et al.

[11] Patent Number: 5,072,626

[45] Date of Patent: Dec. 17, 1991

[54] MEASUREMENT OF ULTRAFINE PARTICLE SIZE DISTRIBUTIONS

[75] Inventors: David S. Ensor, Chapel Hill, N.C.; Gilmore J. Sem, Lauderdale, Minn.

[73] Assignee: Research Triangle Institute, Research Triangle Park, N.C.

[21] Appl. No.: 379,826

[22] Filed: Jul. 14, 1989

[51] Int. Cl.⁵ .............................................. G01N 1/00
[52] U.S. Cl. ..................................... 73/865.5; 356/37
[58] Field of Search ............. 73/863.82, 865.5, 863.31, 73/863.33, 28, 863.22; 356/335, 336, 37, 437, 438, 439

[56] References Cited

U.S. PATENT DOCUMENTS

| | | | |
|---|---|---|---|
| 2,353,828 | 7/1944 | Hyde | 73/28 |
| 3,457,787 | 7/1969 | Maatsch et al. | 73/863.24 |
| 3,678,487 | 7/1972 | Ludewig, Jr. et al. | 73/865.5 |
| 3,709,614 | 1/1973 | Hayakawa | 73/865.5 |
| 3,830,688 | 8/1974 | Mannbro | 162/29 |
| 3,831,452 | 8/1974 | Pittenger | 73/863.82 |
| 4,128,335 | 12/1978 | Haberl et al. | 356/37 |
| 4,182,632 | 1/1980 | Cargill | 127/5 |
| 4,449,816 | 5/1984 | Kohsaka et al. | 356/37 |
| 4,463,595 | 8/1984 | Yeh et al. | 73/28.01 |
| 4,570,494 | 2/1986 | Dunn et al. | 73/863.22 |
| 4,742,718 | 5/1988 | Jimbo | 73/865.5 |
| 4,764,758 | 8/1988 | Skala | 73/865.5 |
| 4,790,650 | 12/1988 | Keady | 356/37 |
| 4,792,199 | 12/1988 | Borden | 356/37 |
| 4,860,598 | 8/1989 | Bailey et al. | 73/863.33 |
| 4,890,481 | 1/1990 | Ezawa et al. | 73/865.5 |

FOREIGN PATENT DOCUMENTS 3737129  5/1989  Fed. Rep. of Germany ...... 356/438

Primary Examiner—Robert Raevis
Attorney, Agent, or Firm—Irving M. Freedman

[57] ABSTRACT

A measurement system for microelectronic clean rooms to measure ultrafine particle size distribution in the range of 0.002 to 0.2 micrometers is provided which includes four screen diffusion stages each connected in series with a condensation nucleus detector. The input to each screen diffusion stage is connected to a localized area to be measured, and the output of each condensation nucleus detector is connected to a vacuum system which simultaneously draws particle bearing air through the four channels. The output signals of the condensation nucleus detectors present particle size distribution. In one embodiment of the present invention, one or more optical particle detectors are connected in parallel with the diffusion stage-condensation nucleus detectors to expand the distribution measurements to larger sizes. Other embodiments include a manifold probe to probe a localized area, an alarm system actuated when particle levels exceed a predetermined level, and a manifold assembly to minimize vacuum lines passing through the walls of the microelectronic clean room.

15 Claims, 2 Drawing Sheets

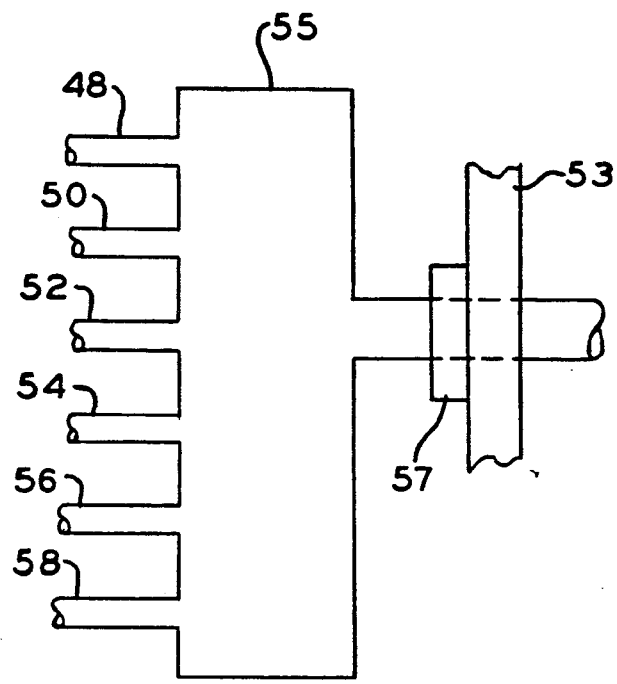
FIG_3
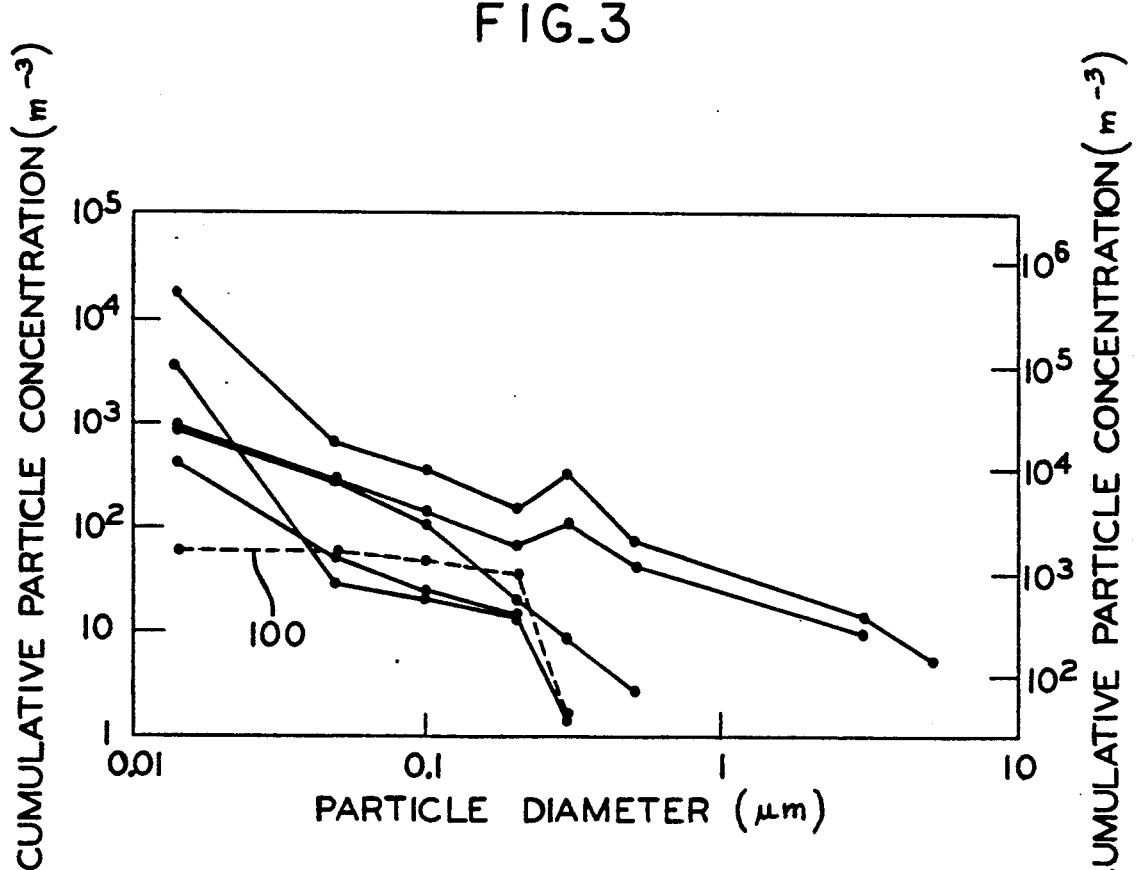
FIG_4

MEASUREMENT OF ULTRAFINE PARTICLE SIZE DISTRIBUTIONS

BACKGROUND OF INVENTION

This invention relates to the measurement of ultrafine particle size distributions, and in particular to measurement equipment useful in measuring the effectiveness of microelectronic manufacturing facility clean room equipment in maintaining the facility to the required or desired freedom from dust particles.

A modern microelectronics clean room requires continuous monitoring to insure that the required air quality is maintained. Microelectronic circuit elements have become so small (into the submicron range) that ultrafine dust particles (those smaller than 0.2 um) can cause circuit failure so it has become necessary to be able to measure ultrafine aerosol particles, at concentrations of less than 100 per cubic foot in order to adequately monitor clean rooms for manufacturing small microelectronic components. These low concentrations of ultrafine particles can not be accurately measured nor their distribution determined by present equipment.

While it is known, for example, to use diffusion batteries to separate various ultrafine particle sizes in an air sample in order to be able to measure the particles, conventional methods of doing so sequentially measure particle populations in size increments. Such an approach is discussed in "Measurement of Nanometer Aerosols" by David Sinclair, *Aerosol Science and Technology*, volume 5, Number 2, 1986, pp. 187-203 which discusses the use of a rotary sequencing valve in combination with a single diffusion battery and a CNC. We have determined that at low concentrations the time required to collect a statistically significant number of particles is so long that the size distribution of the aerosol may change before the measurement in such an approach is complete.

Ultrafine particles are too small to be detected by today's optical particle counters or by laser particle detectors (which cannot detect particles smaller than 0.05-0.1 micrometers). Ultrafine particles can be counted, however, without size classification, by commercial condensation nucleus detectors (CNCs). CNC's operate on the scientific principle that a supersaturated vapor will condense on small particles, forming larger droplets that make detection easier. This phenomena occurs naturally on foggy days or upon the formation of clouds in the atmosphere. One CNC is disclosed and described in U.S. Pat. No. 4,790,650 issued Dec. 13, 1988 to Patricia B. Keady, and assigned to TSI Incorporated, which patent is incorporated herein by reference. Also see "Continuous Flow, Single-Particle-Counting Condensation Nucleus Counter," *Journal of Aerosol Science*, Vol. 11, pp. 343-357 by Jugal K. Agarwal and Gilmore J. Sem.

Prior art proposals have included the use of electrostatic classifiers in combination with CNC detectors. An electrostatic classifier separates particles according to electrical mobility. However, the use of a particle size classifier has not proven to be practical and effective for very low levels of ultrafine particles, again because of long sequential counting times.

None of the various past approaches have provided an adequate measurement of the ultrafine particle size distributions in modern microelectronic circuit fabrication clean rooms. The configuration disclosed in this invention allows measurement of ultrafine particles over extended periods and during short bursts or short term (a few seconds) increases in concentration.

OBJECTS AND SUMMARY OF INVENTION

Accordingly, it is an object of the present invention to provide an improved ultrafine particle size measurement system which is effective at low concentrations of particles.

It is a further object of the present invention to provide an improved ultrafine particle size measurement system which is capable of analyzing short concentration bursts of ultrafine particles.

It is a still further object of the present invention to provide an improved ultrafine particle measurement system which can measure particle contamination in a localized area.

It is a yet further object of the present invention to provide an improved ultrafine particle size measurement system which provides accurate concentration measurements of particles of different sizes.

It is another object of the present invention to provide an improved ultrafine particle measurement system for use in microelectronic circuit fabrication clean rooms with improved accuracy and reliability.

With the aforesaid objects in view, the present invention resides in a measurement system which includes a parallel array of diffusion stages, each with a different cut of particle size, and each with its own condensation nucleus counter (CNC). A vacuum is provided to draw an independent air sample from the localized area of measurement for simultaneous analysis of different size cuts through the multiple parallel diffusion stage and series CNC paths. The outputs of all CNCs are combined to yield a substantially real time particle size distribution. Other embodiments of the present invention include simultaneous analysis of larger size cuts through use of one or more optical particle counters in parallel with the diffusion stages and CNCs, and a manifold to enable all of the counters to be sampling substantially the same localized area at the same time.

BRIEF DESCRIPTION OF DRAWINGS

FIG. 3 shows an exhaust manifold useful in the present invention; and FIG. 4 is a plot of six-minute average particle size distributions in a microelectronics circuit fabrication clean room measured during episodes of particle bursts.

Referring to FIG. 1, a manifold probe 10 includes an inlet 12, a body 8; and a plurality of outlet lines 14, 16, 18, 20, 22 and 24 connected to optical particle counter 30, diffusion stages 32, 34, 36, 38 and optical particle counter 40, respectively. The optical counters 30 and 40 are in turn connected through exhaust lines 48 and 58 to the vacuum system 46. The exhausts of diffusion stages 32, 34, 36 and 38 are connected in turn to condensation nucleus detectors 33, 35, 37, and 39, respectively, which are connected through their exhausts 50, 52, 54 and 56 to the vacuum system 46. The CNCs used were TSI, Inc. model 3760.

Figure 1:
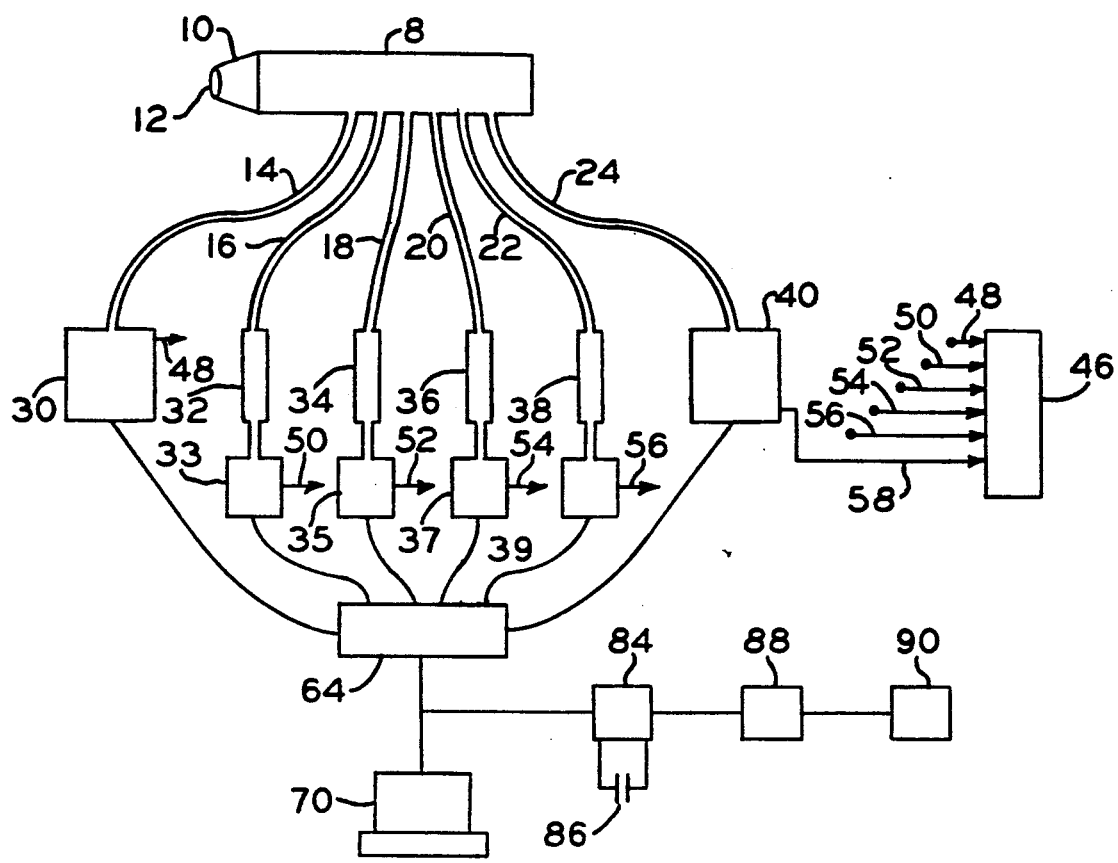
FIG. 1 is a block diagram showing the present invention.

As a result, the vacuum system 46, which is located externally, preferably outside the clean room to remove possible particle generation, creates a vacuum which draws air from the localized area in the region of inlet 12 through the body 8 of manifold 10 where it is distributed in parallel and simultaneously through the optical particle counters 30 and 40; and also simultaneously through diffusion stages 32, 34, 36 and 38 in series with CNCs 33, 35, 37 and 39, respectively. A volume flow rate of 16.8 liters per minute is adequate for the equipment shown in FIG. 1.

The optical particle counters 30 and 40 are provided to extend the range of the size distributions measured, in that they include size cuts at 0.3, 0.5, 3 and 5 micrometers, that is they measure the larger size particles. The optical particle counters may be models 3755 and 3753 sold by TSI, Inc. The optical particle counters directly provide electrical signals representative of the number of particles at their calibrated size cuts, that is the various size cuts act as high pass filters, passing only particles above the preselected size cut. For a description of the operation of such optical particle counters, reference may be had to Sem et al, "New System for Continuous Clean Room Particle Monitoring", 1985 Proceedings of the 31st Annual Technology Meeting of the Institute of Environmental Sciences, pp. 18–21, IES, 940 E. Northwest Highway, Mount Prospect, Ill. 60056. The signals representing the particles measured by the optical particle counters 30 and 40 are provided to the multiplexer 64.

The screen diffusion stages 32, 34, 36 and 38 are provided with 0, 5, 11, and 23 wire screens respectively. As is shown more clearly in the diffusion stage shown in FIG. 2, a selected number of screens are placed across the chamber in the flow path to control the size particles which can flow through.

Figure 2:
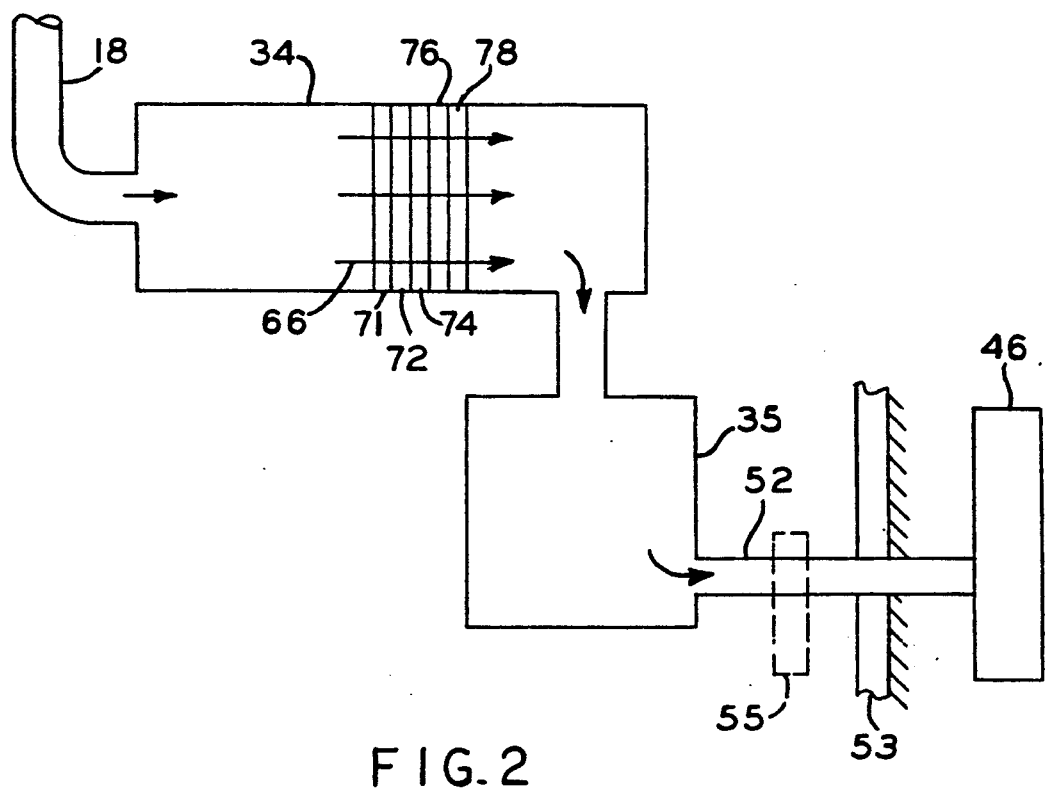
FIG. 2 is a simplified drawing of a diffusion stage of the type useful in the present invention.

Referring to FIG. 2, it is seen that the air flow is through line 18 into the interior of diffusion stage 34 and sequentially through CNC 35 via exhaust 52 through wall 53 to the vacuum system 46. To minimize the number of vacuum lines through wall 53, the exhaust lines 48, 50, 52, 54, 56 and 58 can be combined through a manifold 55 as described below in connection with FIG. 3. The diffusion stage 34 has provisions for inserting a plurality of screens side by side, transverse to the air flow 66. The diffusion stage 34 includes five screens, 71, 72, 74, 76 and 78. The screens may be stainless steel each containing in excess of 14,000 holes. The individual particles in the air flow 66 are in rapid random motion from interactions with air molecules even though they are being forced through the diffusion stage 34 through the action of the vacuum system 46. The smaller particles exhibit the greater random motion and so tend to collect on, or stick to the surface of the screens, such that the smaller sizes are collected, or scaled off, on the screens first, with the larger size particles passing through the screens. The fine mesh diffusion screens thus selectively remove small particles from the aerosol through diffusion, with the set of fine mesh diffusion screens acting to capture small particles Increasing the number of screens increases the capture of larger particles. As a result it is possible to predetermine the particle size cut of the diffusion stages 32, 34, 36 and 38 by the number of screens provided for each battery. Also, by selecting each battery to provide a different size cut it is possible to capture and measure a spectrum, or range, of particles in order to provide the basis for particle size distribution measurements. In one embodiment, the results of which are described below in connection with FIG. 4, diffusion stage 32 was provided with zero screens, that is the particle laden air was allowed to pass through. Diffusion stage 34 was packed with 5 screens, diffusion stage 36 was packed with 11 screens, and diffusion stage 38 was packed with 23 screens. Since the size cut of the screen diffusion stages depends on the number of screens packed into the battery, such an arrangement provides a simultaneous band of ultrafine particle measurements. TSI, Inc. Model 3040 diffusion battery wire screens were used in the embodiment of the present invention described herein.

The optical particle counter 30 was provided with particle size cuts at 0.3 and 3.0 micrometers while particle counter 40 was provided with particle cuts at 0.5 and 5 micrometers.

Increasing the number of diffusion stage condensation nucleus detectors in parallel with those shown in FIG. 1 with different size particle cuts, that is different numbers of screens in the diffusion stages, would provide more detailed particle size distribution measurements. However, the hardware requirements and cost would increase. It was found that four points or cuts of particle size represent a reasonable and practical compromise in cost.

Referring to FIG. 3, an exhaust manifold 55 is shown. The inputs are exhaust lines 48, 50, 52, 54, 56 and 58 from optical particle counter 30, diffusion stages 32, 34, 36 38 and optical particle counter 40, respectively. A connector such as 57 may be installed in the clean room wall 53 to facilitate connection of the measurement system.

Referring again to FIG. 1, the condensation nucleus detectors 33, 35, 37 and 39 provide electrical signals responsive to the particle concentrations in lines 16, 18, 20 and 22 respectively. The signal outputs of the optical particle counters 30 and 40, and the condensation nucleus detectors 33, 35, 37 and 39, are connected through multiplexer 64 which may be model 3701 sold by TSI, Inc. to a personal computer 70. The measurement system is calibrated and programmed to rapidly scan and display or record the outputs of the optical particle counters and condensation nucleus detectors.

The output of the multiplexer 64 is also connected in one embodiment to the accumulator circuit 84 which charges a capacitor in response to the level or concentration of particles reaching multiplexer 64. A voltage source 86 provides a reference or predetermined voltage. If the voltage in the accumulator circuit exceeds the predetermined voltage in a preset time period, the actuator circuit 88 actuates the alarm and/or control circuit 90 to provide an alarm and/or institute a control action. Alternatively, the multiplexer 64 may include an alarm.

In operation, the inlet nozzle 12 of the manifold probe 10 is positioned at a point or localized area where particle size distribution is to be measured. This may, for example, be at a particular location in the microelectronics clean room where a particular process step is resulting in poor device yield. Alternatively, it could be to sample the clean air being provided by the air supply to the clean room. Vacuum system 46 draws air from the location being probed through the lines 14, 16, 18, 20, 22 and 24, and through the particle counting or measuring devices namely optical particle counter 30, diffusion stage and condensation nucleus detector combinations 32-33, 34-35, 36-37 and 38-39, respectively, to the vacuum system 46, through the manifold 55 and through wall 53 of the microelectronic circuit fabrication clean room.

Since each of the particle counting devices, that is, the optical particle counters and the diffusion stage-condensation nucleus counters provide a different particle cut, they act as size classifying devices, and function as adjustable particle filters or band pass filters, and each passes particles larger than its predetermined threshold size.

The particle counters thus simultaneously measure particle populations in parallel channels after they are separated by size into the different channels. Measurement systems which sequentially sample different size particles in low concentrations, whether the particles are obtained by a series or parallel particle separation are essentially sampling each particle size group at different times. This provides the real possibility that at a particular period when a particular size particle is being measured, there may be less (or more) than an average or normal amount of such particles, leading to inaccurate measurements.

An example of the operation of the present invention in measuring the ultrafine particle distribution in an actual microelectronics circuit fabrication clean room is summarized in part by FIG. 4.

FIG. 4 shows the particle size distribution measurements obtained during selected six minute particle bursts, that is short periods during which the particle concentration changes relatively rapidly. FIG. 4 shows a plot of ultrafine particles in the clean room with particle diameter plotted on the X axis and with cumulative particle concentration on the Y axis. The particle concentration is plotted as number per cubic foot, and also as number per cubic meter, with the range of the former being from 1 to 100,000. It is to be noted that the particle diameter measured was in the range of 0.02 to more than 1 micrometers. For comparison, curve 100 is typical of a clean room "at rest" or during periods of low activity. Such bursts may result from bringing idle equipment on line, personnel activity in the clean room or erratic faults in the clean room air cleaning system. The capability of measuring such short bursts according to size over such an ultrafine particle size range has not been found possible with any prior art measuring equipment. The present invention thus makes it possible to measure and isolate ultrafine particle contamination of a random or irregular nature. The portable nature of the probe 10, which can be moved to suspected areas in the clean room to conduct localized ultrafine particle distribution measurements, provides a new and valuable tool in combatting an important problem in state of the art microelectronics clean rooms.

While the present invention has been described with respect to certain preferred embodiments thereof, it is to be understood that numerous variations in the details of construction, the arrangement and combination of parts, and the type of materials used may be made without departing from the spirit and scope of the invention.

What we claim is:

1. A system for measuring ultrafine particle distributions in a gas comprising:
   a particle counting array including a plurality of diffusion stages;
   each of said diffusion stages passing substantially only those particles above a certain predetermined size; and
   a particle counter connected in series with each of said diffusion stages;
   a vacuum system for drawing particle laden gas through each of said diffusion stages, and then through its associated particle counter to which it is connected in series;
   means to connect each of said diffusion stages to substantially the same localized area in order that each of said diffusion stages and its associated particle counters are continuously provided with a portion of similar gas at substantially the same time;
   and means to provide a signal representative of the distribution of particles of various sizes passing at substantially the same time through each of said diffusion stage and its associated particle counter;
   wherein said particle counters are condensation nucleus detectors;
   said diffusion stages are screen diffusion stages each having a different number of screens to provide a different particle-pass filter;
   said particle counter array counts ultrafine particles having a diameter in the range of 0.002 to 0.2 microns; and
   said means to connect said diffusion stages to substantially the same localized area includes a manifold probe comprising an inlet and a plurality of outlets, each of said inlet and outlets being connected directly to an intermediate body to form a manifold, said outlets being separately connected to the upstream end of each of said particle counters and said diffusion stages.

2. The measuring system of claim 1 wherein said plurality of diffusion stages is four, having 1, 5, 11 and 23 screens respectively.

3. The measuring system of claim 1 wherein said particle counting array includes one or more optical particle counters in parallel with said diffusion stages and their series-connected condensation nucleus detectors, such that said one or more optical particle counters are each provided with a portion of the same gas at substantially the same time as each of said diffusion stages and its series-connected condensation nucleus detector.

4. The measuring system of claim 3 wherein said one or more optical particle counters each provide a particle-pass filter to count particles of a larger size than said diffusion stages and associated condensation nucleus detectors.

5. The measuring system of claim 1 wherein said means to provide a signal includes connecting the signals provided by each condensation nucleus detector to an information processor to present substantially real time particle distribution information of the particles included in said gas.

6. The measuring system of claim 5 wherein a multiplexer connects said signals to said information processor and said information processor is a personal computer.

7. The measuring system of claim 6 wherein said system includes an actuator which responds when the particles passing through said particle counting array exceeds a predetermined reference.

8. The measuring system of claim 7 wherein said actuator is connected to an alarm which is activated when said particles exceed said predetermined reference.

9. The measuring system of claim 1 wherein said probe is moveable to enable the measurement of ultrafine particle distribution at selected locations within said microelectronics clean room.

10. The measuring system of claim 1 adapted to measure ultrafine particle distribution in a microelectronics clean room wherein said vacuum system is located outside of the walls of the microelectronics clean room and connected through a wall to said particle counting array.

11. The measuring system of claim 10 wherein a manifold is located within said microelectronics clean room with its input connected to the downstream end of each of said optical particle counters and condensation nucleus detectors, and its single output connected through the wall of said clean room to said vacuum system.

12. A system for monitoring the distribution of ultrafine particles including the range of 0.002 to 0.2 micrometers in a microelectronic circuit fabrication clean room having walls forming an enclosed area comprising:
- a particle size distribution counting array located in said microelectronics circuit fabrication clean room comprising a parallel connection of at least four particle counters;
- each of said particle counters including a screen diffusion stage which is connected in series with a condensation nucleus detector and which performs as a different high pass filter;
- a vacuum system connected to said condensation nucleus detectors;
- said condensation nucleus detectors each being connected to the downstream end of its associated series screen diffusion stage;
- the upstream end of said screen diffusion stages each connected to a localized area such that said vacuum system causes the parallel flow of air from said localized area through each of said particle counters at substantially the same time; and
- means to provide an indication of the distribution of particles in the range of 0.002 to 0.2 micrometers;
- wherein said particle distribution counting array includes one or more optical particle counters connected in parallel with said at least four particle counters to receive a portion of the parallel flow from said localized area at substantially the same time as said at least four parallel connected particle counters;
- said optical particle counters each provide a particle high pass filter outside the range of 0.01 to 0.1 micrometers in order to expand the particle size distribution by said system; and
- said vacuum system is located outside the walls of said microelectronics fabrication clean room.

13. The system of claim 12 wherein the connection of said screen diffusion stage to a localized area includes a manifold probe with an inlet, and an exhaust to each of said particle counters, said probe being portable to enable the particle distribution measurement at selected locations within said microelectronics fabrication clean room.

14. The system of claim 13 wherein said indication means includes a multiplexer and information processor.

15. The system of claim 14 wherein an actuator and alarm is connected to said indication means to provide an alarm when the particles at said localized area exceeds a predetermined level.

* * * * *